(12) United States Patent
Spivey et al.

(10) Patent No.: US 7,771,416 B2
(45) Date of Patent: Aug. 10, 2010

(54) CONTROL MECHANISM FOR FLEXIBLE ENDOSCOPIC DEVICE AND METHOD OF USE

(75) Inventors: James T. Spivey, Cincinnati, OH (US); Omar J. Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 267 days.

(21) Appl. No.: 11/762,855

(22) Filed: Jun. 14, 2007

(65) Prior Publication Data
US 2008/0312506 A1 Dec. 18, 2008

(51) Int. Cl.
*A61B 17/00* (2006.01)
(52) U.S. Cl. .............................. 606/1; 600/106; 600/146
(58) Field of Classification Search .................. None
See application file for complete search history.

(56) References Cited

U.S. PATENT DOCUMENTS

| | | | |
|---|---|---|---|
| 3,470,876 A | 10/1969 | Barchilon | |
| 4,580,551 A | 4/1986 | Siegmund et al. | |
| 5,325,845 A * | 7/1994 | Adair | 600/114 |
| 5,449,021 A | 9/1995 | Chikama | |
| 5,555,883 A | 9/1996 | Avitall | |
| 5,634,466 A | 6/1997 | Gruner | |
| 5,976,075 A | 11/1999 | Beane et al. | |
| 6,033,378 A * | 3/2000 | Lundquist et al. | 604/95.01 |
| 6,179,776 B1 | 1/2001 | Adams et al. | |
| 6,236,876 B1 | 5/2001 | Gruner et al. | |
| 6,491,626 B1 | 12/2002 | Stone et al. | |
| 6,672,338 B1 | 1/2004 | Esashi et al. | |
| 6,749,560 B1 | 6/2004 | Konstorum et al. | |
| 6,780,151 B2 | 8/2004 | Grabover et al. | |
| 7,008,375 B2 | 3/2006 | Weisel | |
| 2002/0177750 A1 | 11/2002 | Pilvisto | |
| 2004/0186350 A1 | 9/2004 | Brenneman et al. | |
| 2004/0199052 A1 | 10/2004 | Banik et al. | |
| 2005/0124855 A1 | 6/2005 | Jaffe et al. | |
| 2005/0131279 A1 | 6/2005 | Boulais et al. | |
| 2006/0015009 A1 | 1/2006 | Jaffe et al. | |
| 2006/0178560 A1 | 8/2006 | Saadat et al. | |
| 2007/0049800 A1 | 3/2007 | Boulais | |

* cited by examiner

*Primary Examiner*—Henry M Johnson, III
*Assistant Examiner*—Lynsey Crandall
(74) *Attorney, Agent, or Firm*—Nutter McClennen & Fish LLP

(57) ABSTRACT

Control devices and methods are provided for controlling tension applied to a tensioning element extending through a flexible shaft, such as on an endoscopic device. In one exemplary embodiment, the methods and devices are configured to allow free movement and optionally provide slack to a control mechanism on an endoscopic device during insertion to allow free flexion of the shaft of the device, and to tension the control mechanism when desired to actuate, articulate, or otherwise control the working end or other portion of the device disposed within a patient's body.

13 Claims, 12 Drawing Sheets

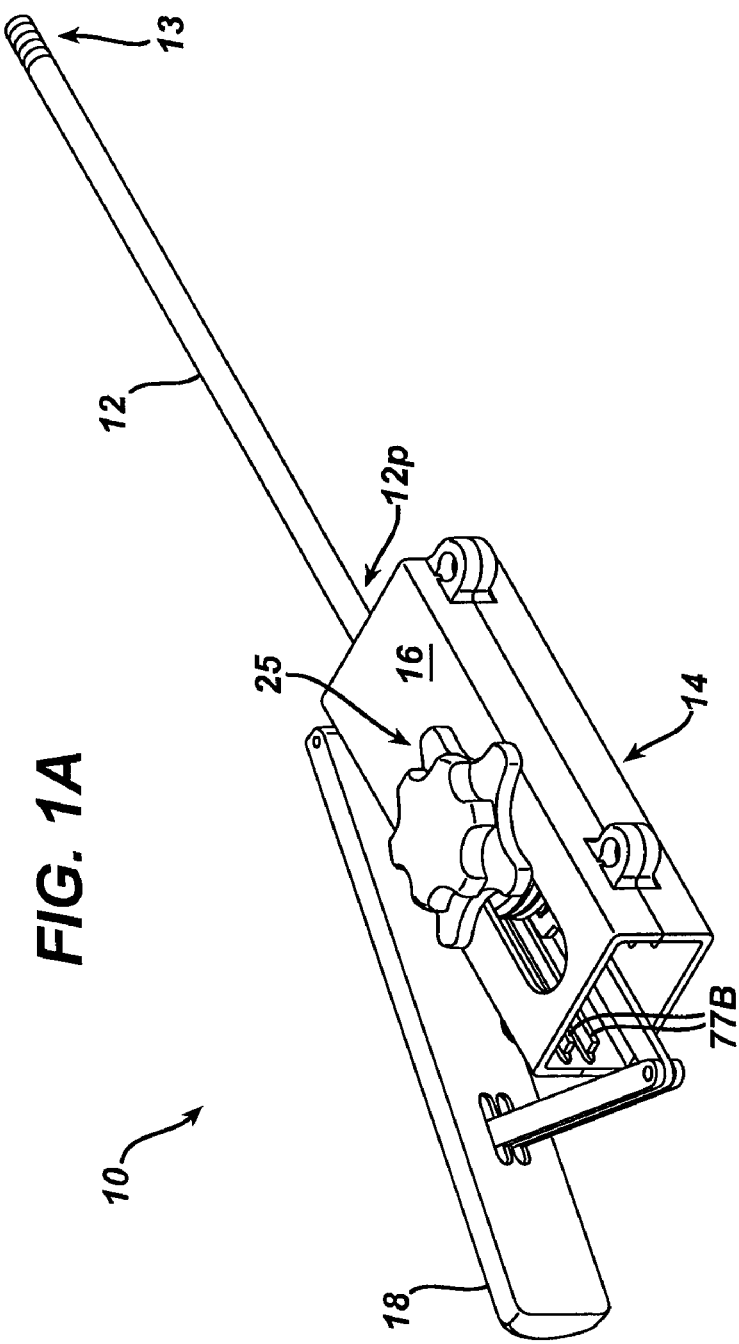

CONTROL MECHANISM FOR FLEXIBLE ENDOSCOPIC DEVICE AND METHOD OF USE

FIELD OF USE

The invention relates to surgical devices and methods of use, and in particular to devices and methods for controlling endoscopic devices.

BACKGROUND

Endoscopic surgical instruments are often preferred over traditional open surgical devices since the use of a natural orifice tends to reduce the post-operative recovery time and complications. Consequently, significant development has gone into a range of endoscopic surgical instruments that are suitable for precise placement of a working end of a tool at a desired surgical site, as well as articulation and/or actuation of various of the working end of the device upon arrival at the treatment site. These tools can be used to engage and/or treat tissue in a number of ways to achieve a diagnostic or therapeutic effect.

Endoscopic surgery requires that the shaft of the device be flexible while still allowing the working end to be articulated to angularly orient the working end relative to the tissue, and to be actuated to treat tissue. The controls for articulating and/or actuating a working end of an endoscopic device tend to be complicated by the elongate nature of the flexible shaft. Generally, the control motions are all transferred through the shaft as longitudinal translations, which can interfere with the flexibility of the shaft. In particular, as the shaft flexes during passage through a tortuous lumen, tension is applied to the control mechanism. This in turn can restrain the flexibility or cause undesired flexing of the shaft. Additionally, control of the working end of such devices is further complicated when utilizing control wires that do not pass through the center of the flexible shaft because the wires become longer or shorter as the shaft is flexed.

Accordingly, there remains a need for improved devices and methods for actuating a working end of a flexible endoscopic surgical device.

SUMMARY

Devices and methods are provided for controlling tension applied to a tensioning element extending through a flexible shaft, such as on an endoscopic device. In an exemplary embodiment, the methods and devices are configured to allow free movement and optionally provide slack to a control mechanism on an endoscopic device during insertion to allow free flexion of the shaft of the device, and to tension the control mechanism when desired to actuate, articulate, or otherwise control the working end or other portion of the device disposed within a patient's body.

In one embodiment, a control mechanism is provided and includes a tensioning element adapted to extend through a flexible elongate shaft of an endoscopic device, and a spool having the tensioning element coupled thereto. The spool can be movable between a first position in which the spool provides slack to the tensioning element, and a second position in which the spool engages the tensioning element such that movement of the spool is effective to tension the tensioning element.

The spool can have a variety of configurations. In one exemplary embodiment, the spool can include a pair of opposed plates with a plurality of posts extending therebetween for movably coupling the pair of plates. The tensioning element can be at least partially disposed around the posts. The spool can also include a biasing element (e.g., a wave spring) disposed between each pair of plates and adapted to bias the plates to one of the first and second positions (e.g., an open position).

The control mechanism can also include a variety of features for moving the spool between the first and second positions. In one embodiment, the control mechanism can include a driver disposed adjacent to the spool and adapted to move the spool between the first and second positions. The spool can include opposed plates that are spaced apart from one another in the first position (i.e., the open position), and that move together to engage the tensioning element in the second position (i.e., the closed position), and the driver can include at least one wedge element slidably disposed relative to the opposed plates. In one exemplary embodiment, the wedge element(s) can be slidably disposed between a pair of spreader plates movably coupled to one another, and sliding movement of the wedge can be effective to move the pair of spreader plates toward and away from one another to thereby move the opposed plates between the first and second positions. The control mechanism can also include a trigger coupled to the wedge and disposed on a housing containing the spool and the wedge therein. The trigger can be adapted to slidably move the wedge. The spool can also be slidably disposed within a housing to provide slack to the tensioning element. Additionally, the control mechanism can include a control member coupled to the spool and adapted to rotate the spool to move the tensioning element when the spool is in the second position. For example, the control member can be a rotatable knob fixedly coupled to the spool.

In another embodiment, the control mechanism can include first and second spools, and first and second tensioning elements. A driver can be disposed between the first and second spools and it can be adapted to move the first and second spools between the first and second positions. The driver can be, for example, a wedge slidably disposed between the first and second spools and adapted to move a first plate member on each of the first and second spools toward and away from a second plate member on each of the first and second spools.

In yet another embodiment, an endoscopic device is provided and includes a flexible elongate shaft adapted to be inserted through a tortuous body lumen, a tensioning element extending through the flexible elongate shaft, and an actuator coupled to the tensioning element and movable between a first position in which the actuator is adapted to allow free movement of the tensioning element to thereby allow the flexible elongate shaft to freely move and/or flex, and a second position in which the actuator is adapted to engage the tensioning element such that tension can be applied to the tensioning element.

The device can also include at least one control member coupled to the actuator and adapted to cause the actuator to apply tension to the tensioning element when the actuator is in the second position. In one exemplary embodiment, the device can include a first control member coupled to the actuator and adapted to effect articulation of the flexible elongate shaft in a first plane, and a second control member coupled to the actuator and adapted to effect articulation of the flexible elongate shaft in a second plane that extends substantially transverse to the first plane.

In another embodiment, the tensioning element can include a first wire extending between the actuator and a distal end of the flexible elongate shaft, and a second wire extending between the actuator and the distal end of the flexible elongate shaft. The first wire can be adapted to articulate the flexible elongate shaft in a first plane when tension is applied thereto, and the second wire can be adapted to articulate the flexible elongate shaft in a second plane that extends substantially transverse to the first plane when tension is applied thereto. In an exemplary embodiment, the first and second wires can be adapted to rotate freely relative to the actuator when the actuator is in the first position, and the actuator can engage the first and second wires when the actuator is in the second position.

In yet another embodiment, the actuator can include a first pair of plates having the first wire extending therebetween. The first pair of plates can be spaced a distance apart from one another in the first position to allow free movement of the first wire, and the plates can be moved toward one another in the second position to engage the first wire. The actuator can also include a second pair of plates having the second wire extending therebetween. The second pair of plates can be spaced a distance apart from one another in the first position to allow free movement of the second wire, and the plates can be moved toward one another in the second position to engage the second wire. The actuator can also include a driver disposed between the first and second pair of plates and adapted to move the first and second pair of plates between the first and second positions. The driver can be, for example, a wedge slidably disposed between the first and second pair of plates. In an exemplary embodiment, the wedge is disposed within first and second spreader plates movably coupled to one another and disposed between the first and second pair of plates. For example, the first and second spreader plates can include a cavity formed therebetween for slidably seating the wedge. The cavity can include a first ramped portion for seating a first pair of opposed ramped surfaces formed on the wedge, and a second ramped portion for seating a second pair of opposed ramped surfaces formed on the wedge. The endoscopic device can also include a trigger coupled to the wedge and adapted to slidably move the wedge to thereby move the actuator between the first and second positions. The actuator can also be slidably disposed within a housing and movement of the trigger can be effective to slide the actuator within the housing.

The endoscopic device can also include a first control member coupled to the first pair of plates and effective to rotate the first pair of plates to effect articulation of the flexible elongate shaft in a first plane, and a second control member coupled to the second pair of plates and effective to rotate the second pair of plates to effect articulation of the flexible elongate shaft in a second plane that extends transverse to the first plane.

Exemplary methods for controlling tension applied to a flexible endoscopic device are also provided. In one embodiment the method can include inserting a flexible endoscopic device through a tortuous body lumen. A distal portion of the flexible endoscopic device can have a tensioning element coupled thereto for controllably actuating the flexible endoscopic device, and an actuator coupled to the tensioning element. The actuator can be positioned in a first position during insertion to provide slack to the tensioning element. The method can also include moving the actuator to a second position to cause the actuator to engage the tensioning element, and actuating the actuator to apply tension to the tensioning element.

In one embodiment, moving the actuator to the second position can include pulling a trigger to move a driver disposed adjacent to the actuator. Pulling the trigger can also be effective to slidably move the actuator within a housing to take up the slack in the tensioning element. In another embodiment, actuating the actuator can include rotating a control member coupled to the actuator to rotate the actuator and thereby rotate the tensioning element. In other aspects, the tensioning element can include a first control wire that articulates at least a portion of the flexible elongate shaft in a first plane, and a second control wire that articulates at least a portion of the flexible elongate shaft in a second plane that extends substantially transverse to the first plane.

BRIEF DESCRIPTION OF THE DRAWINGS

Exemplary embodiments of the invention will be more fully understood from the following detailed description taken in conjunction with the accompanying drawings, in which:

FIG. 1A is an isometric view of one embodiment of an endoscopic device having a control mechanism;

DETAILED DESCRIPTION

Figure 1B:
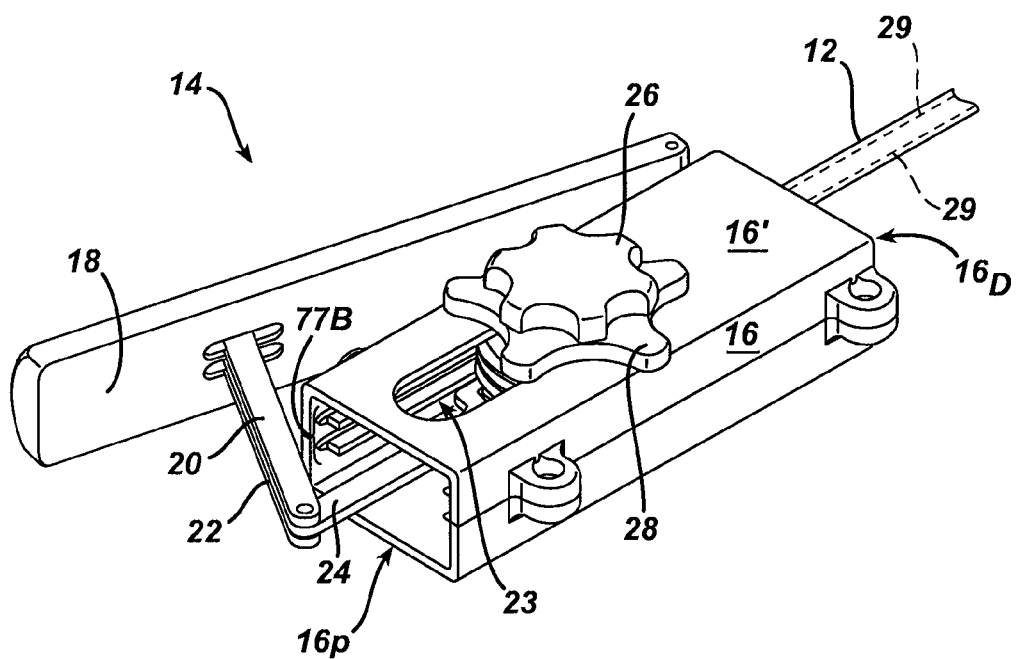
FIG. 1B is an isometric view of a handle of the device of FIG. 1A.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides a control mechanism adapted to control tension applied to a tensioning element extending through a flexible shaft, such as a flexible endoscopic device. In an exemplary embodiment, the control mechanism includes an actuator that is movable between first and second positions so as to engage and disengage a tensioning element extending through a flexible shaft. In the first position (i.e., the disengaged state), the actuator can allow free movement of, and optionally provide slack to, the tensioning element. This will allow the flexible shaft to flex freely en route to the treatment site without interference from the tensioning element. In the second position (i.e., the engaged state), the actuator can engage and apply tension to the tensioning element to actuate, articulate, or otherwise effect movement of a portion of the device.

A person skilled in the art will appreciate that the tensioning element(s) can be used to effect a variety of actions, including actuation (e.g., firing, open/closing jaws, etc.) and articulating (e.g., flexion or steering) of various portions of the device. Thus, while the embodiments disclosed and illustrated herein include tensioning elements that are used for articulating a distal portion of an elongate shaft, the tensioning elements can be used to effect various actions and are not intended to be limited to articulation. The particular action achieved can vary based on the type of device that the control mechanism is used with, and the control mechanism can be incorporated into virtually any device that utilizes a tensioning element extending along at least a portion of a length thereof for translating motion to achieve a particular action. Exemplary devices include, by way of non-limiting example, various flexible insertion devices including endoscopes, catheters, trocars, cannulas, endoscopic staplers and clip appliers, graspers, forceps, hemostatic devices, suturing devices, stiffening or retracting devices, etc. The control mechanism is particularly effective, however, for use with devices that have tensioning elements that do not extend along the central axis of the device, but rather that are offset from the central axis such that flexion of the device causes the tensioning element(s) to shorten or lengthen.

Figure 1C:
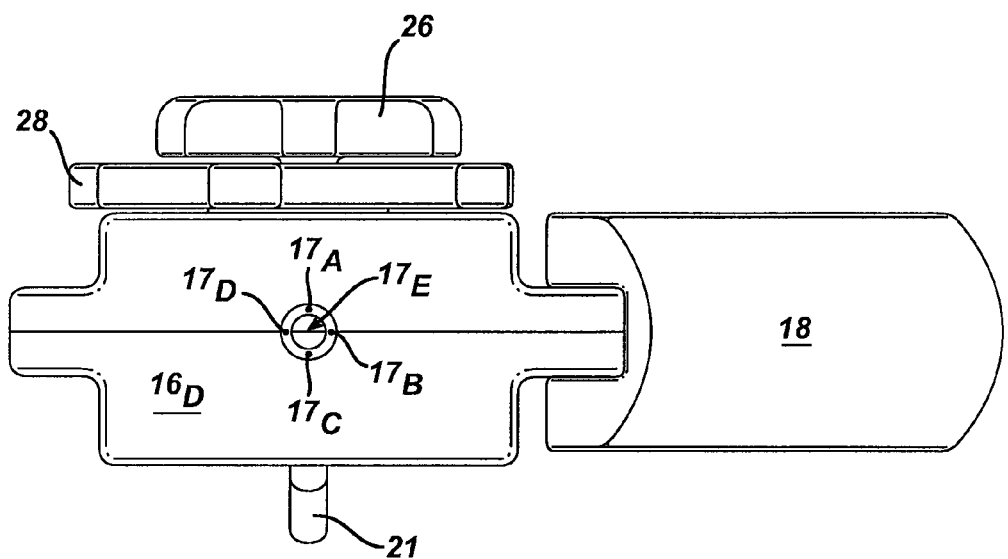
FIG. 1C is a front view of the handle of FIG. 1B.

FIGS. 1A-1C illustrate one embodiment of an endoscopic device 10 having an exemplary control mechanism for selectively controlling articulation of a distal portion of the device 10. In general, the device 10 includes an elongate shaft 12 having a distal portion 13 adapted to be inserted into a patient's body, and a proximal end 12p coupled to a handle 14 adapted to remain external to a patient's body. The control mechanism can include one or more tensioning elements extending between an actuator 25 and the distal portion 13 of the shaft 12 to allow for controlled articulation of the working end of the device 10 (e.g., articulation of the distal portion 13 of the shaft 12). The actuator 25 can be disposed within the handle 14, and a trigger 18 can be coupled to the actuator 25. The handle 14 can also include an outer housing 16 that houses at least a portion of the actuator 25 and that has the trigger 18 formed thereon or mated thereto. In use, the trigger 18 can be actuated to move the actuator 25 between first and second positions. In the first position, i.e., the disengaged position, the actuator 25 can be disengaged from the tensioning element(s) to allow the tensioning element(s) to move freely relative thereto. This will allow the elongate shaft 12 to flex as it is inserted through a tortuous body lumen without interference from the tensioning element(s). In the second position, i.e., the engaged position, the actuator 25 can engage the tensioning element(s) and the actuator 25 can then be used to apply tension to the tensioning element(s) to articulate the distal end of the device. Again, as noted above, while the illustrated embodiment includes tensioning elements adapted to articulate the distal end of the shaft, the tensioning elements can be used to achieve other actions including actuation of an end effector, etc.

As indicated above, the elongate shaft 12 of the device 10 can have a variety of configurations, and it can be in the form of an endoscope, an accessory channel, or any other insertion device. The particular configuration of the shaft 12 can vary depending on the type of procedure being performed and the access technique used. For example, endoscope procedures, in which the shaft 12 is inserted through a natural orifice, require the shaft 12 to be at least partially flexible and to have a relatively long length. The diameter will vary depending on the size of the orifice and body lumen. Laparoscopic procedures, on the other hand, do not require such long shafts, but rather tend to have shorter lengths. Laparoscopic shafts can also be rigid or flexible. A person skilled in the art will appreciate that the shaft 12 can be adapted for use in endoscopic, laparoscopic, open procedures, and combinations thereof.

Figure 2A:
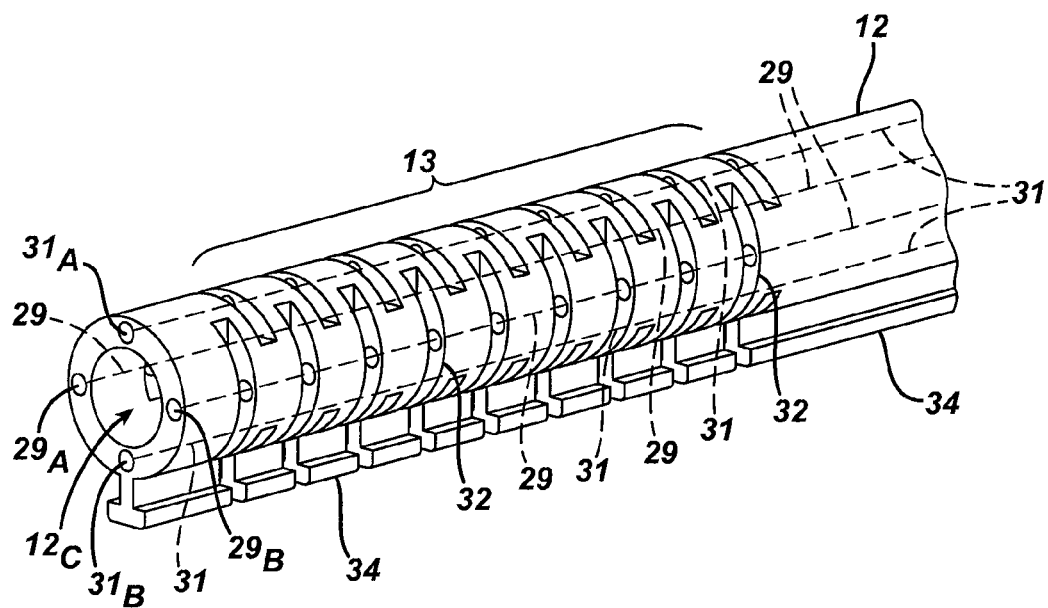
FIG. 2A is an isometric view of a distal end of an elongate shaft of the device of FIGS. 1A-1B.

In an exemplary embodiment, at least a portion of the shaft 12 is flexible to allow the shaft 12 to be flexed in various directions during use. FIG. 2A illustrates one exemplary embodiment of a distal portion 13 of the shaft 12 of FIG. 1A in more detail. As shown, the distal portion 13 has a region of greater flexibility as compared to the remainder of the shaft 12. This will allow tension to be directed to the distal portion 13 and thus will facilitate articulation of the working end. The flexible distal portion 13 can be formed using various techniques, such as by incorporating a more flexible material relative to the remaining length of the shaft 12, by having a relatively smaller diameter as compared to adjacent regions of the shaft 12, and/or by incorporating a plurality of slits 32, as shown, along the length of the flexible distal portion 13. FIG. 2A also illustrates a mating element for mating the shaft 12 to an insertion device. Thus, in this embodiment, the shaft 12 is in the form of an accessory channel that is adapted to extend along and slidably couple to an external surface of an endoscope, or to an external surface of a sheath disposed over an endoscope, and that is adapted to receive various devices therethrough. The particular configuration of the mating element can vary, but in the illustrated embodiment the shaft 12 includes an engagement channel 34 adapted to slide into a corresponding groove or track formed in an insertion device, such as a sleeve disposed around an endoscope. Exemplary accessory channels are described in more detail in U.S. Publication Nos. 2003/0176766, 2003/0176767, 2004/0230095, 2004/0230096, and 2004/0230097, each of which is herein incorporated by reference in its entirety.

As indicated above, the device 10 can also include one or more tensioning elements 29, 31 that extend between the actuator 25 and a portion of the shaft 12 to be articulated, e.g., the flexible distal portion 13. The tensioning element can be any element capable of coupling the actuator 25 to a portion of the shaft 12 to be manipulated, such as the distal portion 13 of the shaft 12 (or an end effector located on the distal end of the shaft), and further capable of being tensioned to articulate (or otherwise effect action of) the distal portion 13. For example, the tensioning element can be a wire, a cable, a fiber, etc. In an exemplary embodiment, as shown in FIG. 2A, the device 10 includes two tensioning elements 29, 31, each being substantially U-shaped with first and second terminal ends $29_A$, $29_B$, $31_A$, $31_B$ that are mated to the distal-most end of the shaft 12 and a central portion (i.e., any portion between the first and second ends) that is coupled to the actuator 25, as will be discussed below. Such a configuration will allow for a desired articulation of the distal portion 13 of the shaft 12 by selectively applying an articulation force via the actuator 25 to either the first end $29_A$, $31_A$ or the second end $29_B$, $31_B$ of each tensioning element 29, 31. In an exemplary embodiment, the first and second ends $29_A$, $29_B$ of the first tensioning element 29 are engaged substantially opposite to one another at the distal-most end of the shaft 12 thereby allowing the flexible distal portion 13 of the shaft 12 to be articulated (e.g., to the left or to the right) within a first plane of movement, and the first and second ends $31_A$, $31_B$ of the second tensioning element 31 are engaged substantially opposite to one another, and offset from the ends $29_A$, $29_B$ of the first tensioning element 29, at the distal-most end of the shaft 12 thereby allowing the flexible distal portion 13 of the shaft 12 to be articulated (e.g., to the left or to the right) within a second plane of movement that extends transverse to the first plane of movement. In an exemplary embodiment, the four ends $29_A$, $29_B$, $31_A$, $31_B$ are positioned so as to be substantially equidistant from each other around the circumference of the distal end of the shaft 12 such that the distal end can be articulate in first and second planes that are substantially orthogonal to one another, i.e., offset about 90°. A person skilled in the art will appreciate that the device 10 can include any number of tensioning elements to move the distal end in any number of directions. Moreover, each tensioning element can have a linear configuration, rather than a U-shaped configuration, with a terminal end that is coupled to the actuator.

Figure 2B:
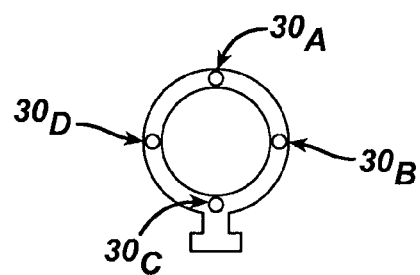
FIG. 2B is a front view of the elongate shaft of FIG. 2A.

In order to allow movement of the tensioning elements 29, 31 to articulate (or otherwise effect action of) the distal portion 13 of the shaft 12, the tensioning elements 29, 31 can be slidably coupled to the shaft 12. While various mating techniques can be used to allow slidable movement of the tensioning elements 29, 31, in one embodiment the walls of the shaft 12 can include a number of lumens extending between proximal and distal ends thereof and sized to allow the tensioning element(s) 29, 31 to slidably extend therethrough. FIGS. 2A and 2B illustrate four lumens $30_A$, $30_B$, $30_C$, $30_D$ for receiving opposed ends of the two U-shaped tensioning elements 29, 31 (which are indicated by dashed lines in FIG. 2A). The distal ends $29_A$, $29_B$, $31_A$, $31_B$ of each tensioning element 29, 31 can be mated to the distal-most end of the shaft 12 using a variety of techniques. For example, the first and second ends $29_A$, $29_B$, $31_A$, $31_B$ of each tensioning element 29, 31 can include a ball-shaped element (not shown) having a diameter that is larger than a diameter of the lumen $30_A$, $30_B$, $30_C$, $30_D$. The ball-shaped element will thus prevent the distal ends $29_A$, $29_B$, $31_A$, $31_B$ of the tensioning elements 29, 31 from being pulled into the lumens $30_A$, $30_B$, $30_C$, $30_D$. Those skilled in the art will appreciate that various other mechanisms can be used to mate the ends of the tensioning elements 29, 31 to the distal-most end of the shaft 12. Moreover, the ends of the tensioning elements 29, 31 can be mated at other locations depending on the particular region of the shaft 12 to be articulated. The proximal U-shaped end of each tensioning element 29, 31 can be positioned within a handle housing 16, and thus the housing 16 can include four openings $17_A$, $17_B$, $17_C$, $17_D$ (shown in FIG. 1C) formed therein and axially aligned with the lumens $30_A$, $30_B$, $30_C$, $30_D$ in the shaft 12 to allow the tensioning elements 29, 31 to exit the shaft 12 and extend into the housing 16. Additionally, a central lumen 12c in the shaft 12 can also be axially aligned with a working channel lumen $17_E$ of the housing 16 which extends to a working channel port 21 capable of introducing various tools through the shaft 12 to the treatment site. In those embodiments in which the tensioning element(s) is configured to actuate an end effector, those skilled in the art will appreciate that the distal end(s) of the tensioning element(s) can be coupled to the end effector using various techniques known in the art.

Figure 3A:
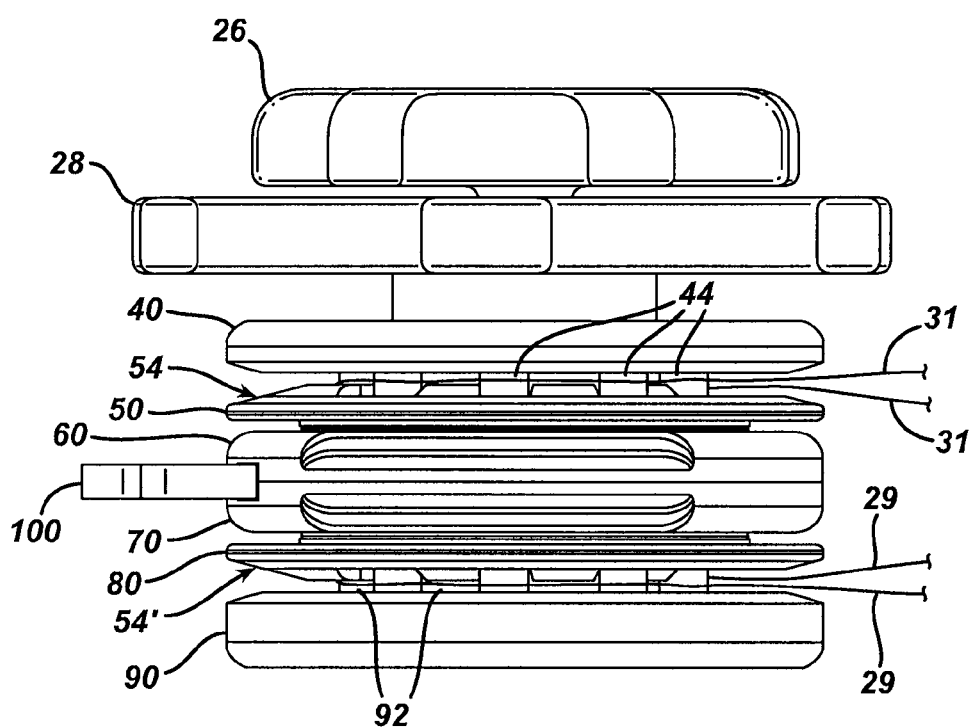
FIG. 3A is a side view of an actuator of the device of FIGS. 1A-1B.
Figure 3B:
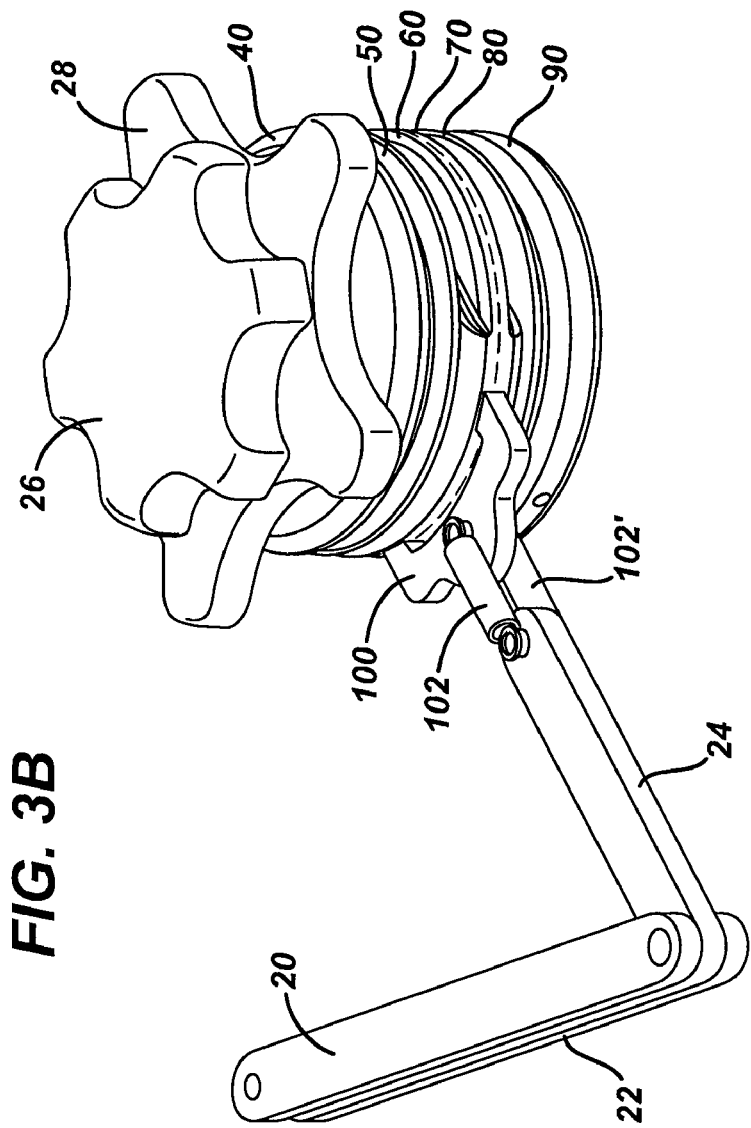
FIG. 3B is an isometric view of the actuator of FIG. 3A showing a trigger coupled thereto.
Figure 3C:
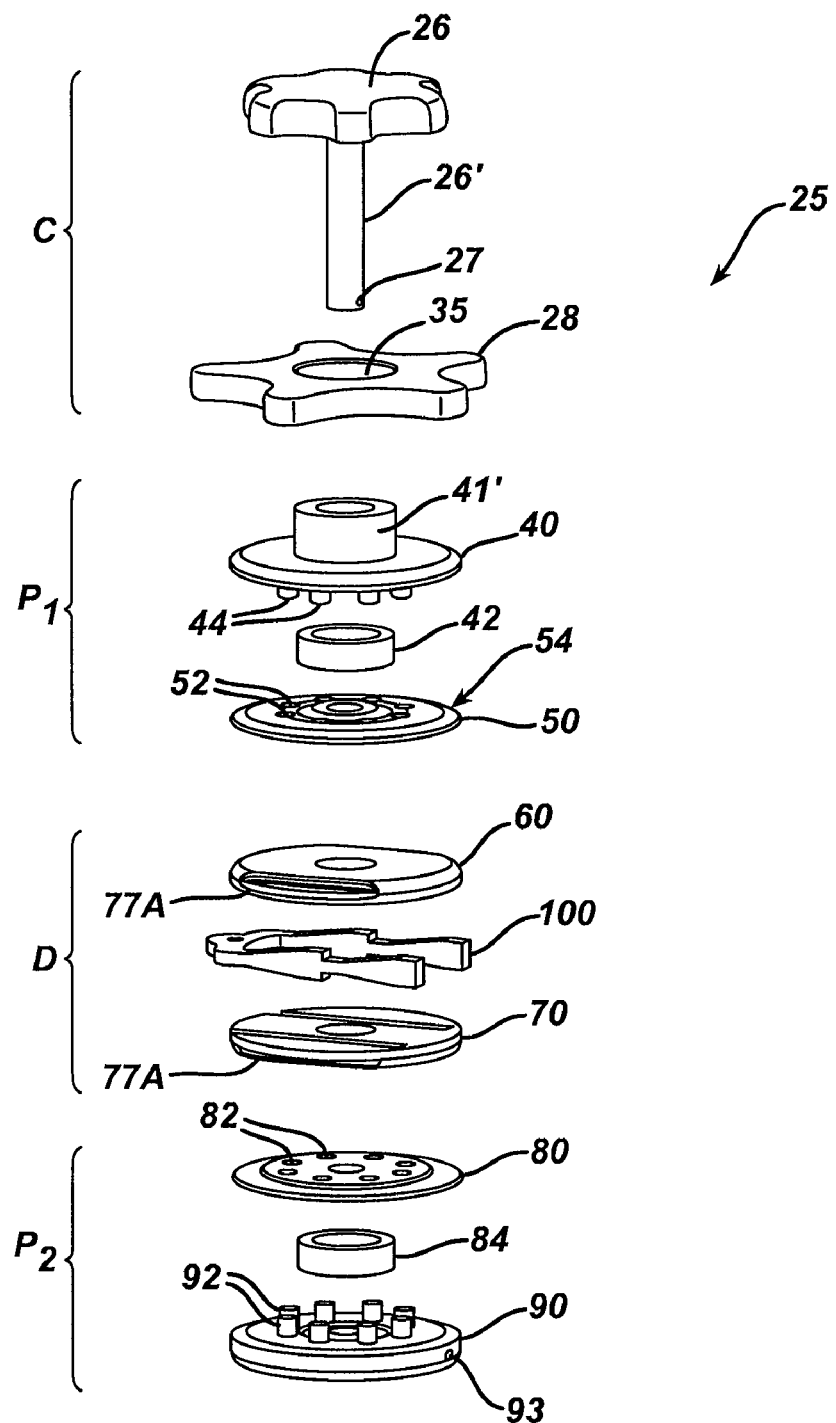
FIG. 3C is an exploded view of the actuator of FIG. 3A.
Figure 3D:
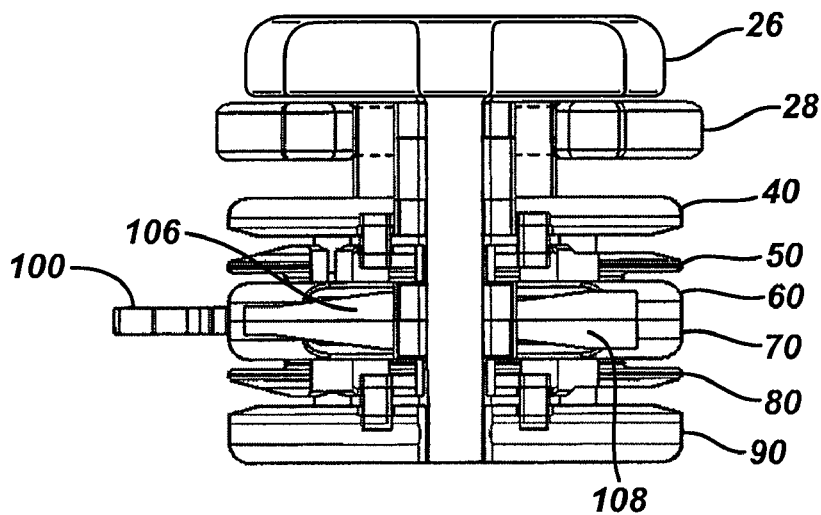
FIG. 3D is a cross-sectional view of the actuator of FIG. 3A.
Figure 3E:
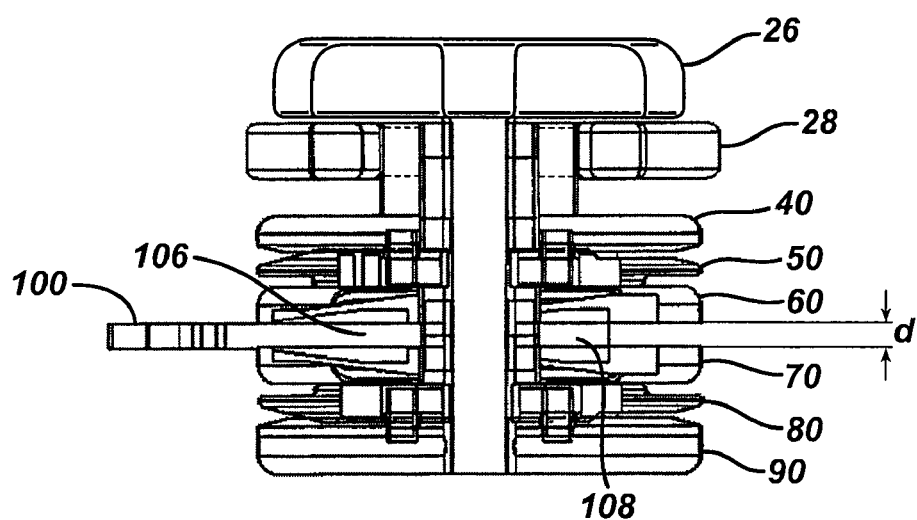
FIG. 3E is another cross-sectional view of the actuator of FIG. 3A.

As mentioned above, the control mechanism can include an actuator 25 which can be manipulated between first and second positions so as to engage and disengage the tensioning element(s) 29, 31. In the first position (i.e., the disengaged state), the tensioning elements 29, 31 can move freely relative to the actuator 25 to allow the shaft 12 to flex freely en route to the treatment site. The actuator 25 can also be configured to provide slack to the tensioning elements 29, 31 in the first position, as will be discussed in more detail below. In the second position (i.e., the engaged state), the actuator 25 can engage and apply tension to the tensioning elements 29, 31 to articulate the distal portion 13 of the shaft 12 in a desired direction. FIGS. 3A-3F illustrate one embodiment of an exemplary actuator 25. As best shown in FIG. 3C, the actuator 25 can be configured as a spool or spool-like element having a first spool member $P_1$ configured to receive the first tensioning element 31, and a second spool member $P_2$ configured to receive the second tensioning element 29. The actuator 25 can also include a drive mechanism D adapted to move the spool members $P_1$, $P_2$ between open and closed positions for releasing and engaging the tensioning elements, and a control mechanism C for controlling the spool members $P_1$, $P_2$ when the spool members $P_1$, $P_2$ are in the engaged positions so as to selectively move the tensioning elements 29, 31. A person skilled in the art will appreciate that the actuator 25 can include any number of spool members for receiving a corresponding number of tensioning elements.

Each spool member $P_1$, $P_2$ can have a variety of configurations, but in an exemplary embodiment each spool member $P_1$, $P_2$ include first and second opposed plates 40, 50, 80, 90 that are adapted to receive the tensioning elements 31, 29, respectively, therebetween. Each plate 40, 50, 80, 90 can have various shapes and/or dimensions. As shown in FIG. 3C, the plates 40, 50, 80, 90 are substantially circular. As for dimensions, those skilled in the art will appreciate that plates 40, 50, 80, 90 having a wide range of diameters and/or thickness are within the spirit and scope of the present invention. Additionally, the plates 40, 50, 80, 90 can be configured in various ways so as to facilitate receipt of the tensioning elements 31, 29 therebetween. In the illustrated embodiment, each pair of plates 40, 50, 80, 90 includes one stationary plate 40, 90 having a plurality of posts 44, 92 extending therefrom, and an opposed movable plate 50, 80 having a series of corresponding openings 52, 82 adapted to receive the posts 44, 92. The posts 44, 92 can be positioned in a circular pattern around an outer portion of each plate 40, 90 for receiving the U-shaped end of the tensioning element 29, 31 therearound, and the openings 52, 82 can be similarly disposed in a circular pattern around an outer portion of each stationary movable plate 50, 80. While not shown, the plates 40, 50, 80, 90 can also include additional features to prevent a slackened tensioning element 31, 29 from becoming disengaging with the pair of opposed plates 40, 50, 80, 90 (i.e., falling out from between the plates 40, 50, 80, 90). For example, an outer-most edge of the opposed plates 40, 50, 80, 90 can include a second set of posts or a housing (not shown) and the tensioning elements 29, 31 can extend between the two sets of posts (or the posts and the housing). Those skilled in the art will appreciate that various other techniques can be used to retain the tensioning elements 31, 29 between the plates 40, 50, 80, 90.

The plates 40, 50, 80, 90 can also include other features to facilitate receipt of the tensioning elements 31, 29 therebetween. For example, as best shown in FIG. 3A, an outer perimeter of at least one of plates of each pair (e.g., the movable plates 50, 80) can include a ramped portion 54, 54' which facilitates receipt of the tensioning elements 31, 29 therebetween. Additionally, the surface of any of the plates 40, 50, 80, 90 which contacts the tensioning elements 31, 29 can include various features, such as surface features, a roughening, a chemical treatment, etc., capable of assisting in securing the tensioning elements 31, 29 to the plates 40, 50, 80, 90. Those skilled in the art will appreciate that any techniques can be utilized to better contact and/or secure the tensioning elements 31, 29 between the opposed plates 40, 50, 80, 90.

The plates 40, 50, 80, 90 can also be movably coupled to one another to allow the plates 40, 50, 80, 90 to engage and disengage the tensioning elements 31, 29. In an exemplary embodiment, the plates 40, 50, 80, 90 are movable between a biased, open position, shown in FIG. 3E, in which the plates 40, 50, 80, 90 are spaced a distance apart from one another to allow free slidable movement of the tensioning elements 31, 29 therebetween, and a closed position, shown in FIG. 3D, in which the plates 40, 50, 80, 90 are moved together to engage the tensioning elements 31, 29 therebetween so as to prevent free movement of the tensioning elements 31, 29. Those skilled in the art will appreciate that each pair of plates 40, 50, 80, 90 can be moved from the biased, open position to the closed position using various techniques. In the illustrated embodiment, a biasing element, such as a wave spring 42, 84 (FIG. 3C), can be disposed between each pair of plates 40, 50, 80, 90 so as to bias each pair 40, 50, 80, 90 apart from one another to an initial open position. In response to an actuation force greater than the force supplied by the biasing element 42, 84, the movable plate 50, 80 of each pair of plates 40, 50, 80, 90 can slide along the respective plurality of posts 44, 92 towards the opposed stationary plate 40, 90 to engage the tensioning element 29, 31 disposed therebetween. In other embodiments, the pairs of plates 40, 50, 80, 90 can be mounted such that all four plate move in response to the actuation force.

Figure 3F:
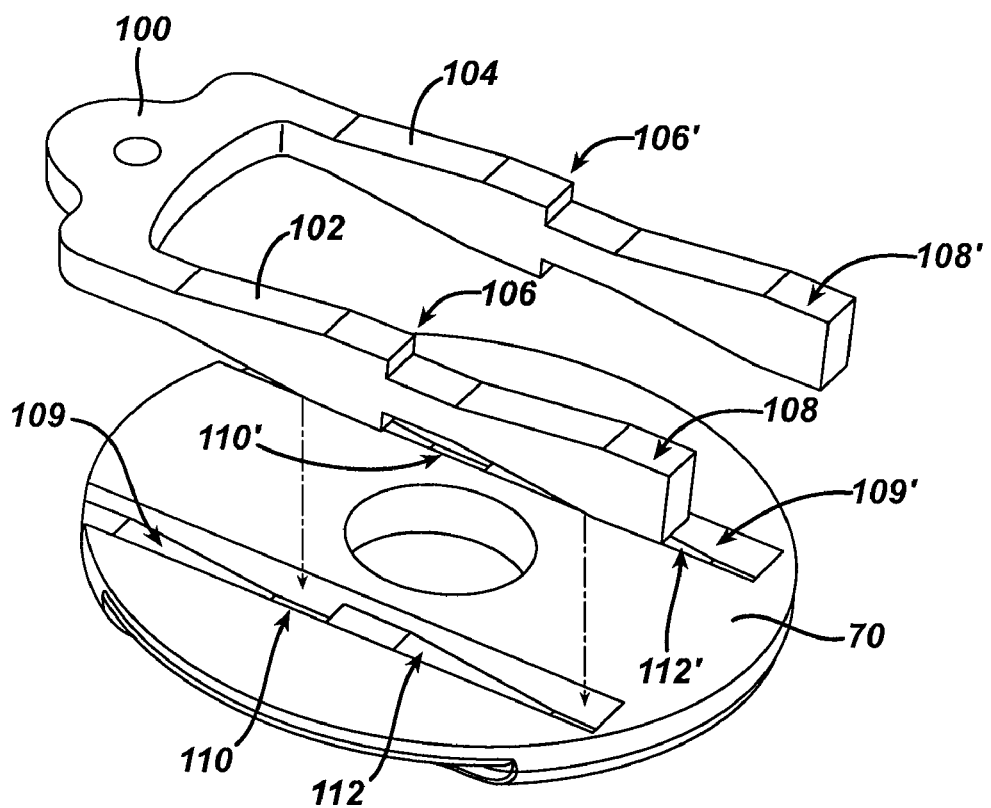
FIG. 3F is an exploded view of a driver and a spreader plate of the actuator of FIG. 3A.

As indicated above, the actuator 25 can also include a drive mechanism D adapted to move the first and second spool members $P_1$, $P_2$ between the disengaged (open) and engaged (closed) positions. In general, the drive mechanism D can be any mechanism configured to apply a force to one or both plates of each pair of opposed plates 40, 50, 80, 90 to overcome the biasing force. In an exemplary embodiment, the drive mechanism D is movably disposed between the movables plates 50, 80 of each pair of plates 40, 50, 80, 90 to push the movable plates 50, 80 toward the stationary plates 80, 90 and into the closed position. In the illustrated embodiment, the drive mechanism D includes a set of spreader plates 60, 70 disposed between the pairs of opposed plates 40, 50, 80, 90, and a wedge 100 disposed between the spreader plates 60 70. Referring to FIGS. 3A-3E, a first spreader plate 60 can be positioned immediately below the first movable plate 50 and a second spreader plate 70 can be positioned immediately above the second movable plate 80. The spreader plates 60, 70 can be adapted so as to slidably receive the wedge 100 therebetween. FIG. 3F illustrates spreader plate 70, however spreader plate 60 can have a similar configuration. As shown, the spreader plate 70 can include a first cavity 109 and a second cavity 109' adapted to slidable seat a first extension 102 and a second extension 104 of the wedge 100. Additionally, the first extension 102 of the wedge 100 can include first and second ramped elements 106, 108 formed thereon, and the second extension 104 of the wedge 100 can also include first and second ramped elements 106', 108' formed thereon. The first cavity 109 of the spreader plate 70 can include a first ramped portion 110 and a second ramped portion 112, and the second cavity 109' can also include first and second ramped portions 110', 112'. As clearly illustrated in FIGS. 3D and 3E, as the wedge 100 is pulled in a proximal direction, each ramped element 106, 108 is pulled into the corresponding ramped portion 110, 112 thereby forcing the spreader plates 60, 70 a distance d apart from one another. The movable plates 50, 80 will move the same distance towards their respective opposed stationary plates 40, 90. As a result, the tensioning elements 29, 31 extending between the plates 40, 50, 80, 90 will be engaged by an interference or compression fit between the two plates 40, 50, 80, 90. One skilled in the art will appreciate that any number and/or orientation of ramps, cavities, drivers, spreader plates, etc. are within the spirit and scope of the present invention. As illustrated in the exemplary embodiment discussed above, strategic placement of the ramped elements and/or cavities can provide added stability to the control mechanism (i.e., placing the ramped elements symmetrically about a central position of the spreader plates 60, 70.) However, any such positioning can be utilized (e.g., a single ramp element placed in communication with any location of the spreader plate(s)). Additionally, in other embodiments, the movable plates 50, 80 themselves can be adapted to receive the ramped elements thereby eliminating the spreader plates.

In order to move the wedge 100 relative to the spreader plates 60, 70, the actuator 25 can further include a trigger 18 adapted to actuate the drive mechanism. In an exemplary embodiment, the trigger 18 is adapted to supply a proximal force to the driver D thereby pulling the wedge 100 to pull the ramped elements 106, 108 into the corresponding ramped portions of the cavities of the spreader plates 60, 70 to drive the spreader plates 60, 70 apart from one another. Various types of triggers can be utilized. FIGS. 1B and 3B illustrate two linking elements 102, 102', in the form of springs, that are coupled at a first end to the wedge 100 and at a second end to a first linkage arm 24. The other end of the first linkage arm 24 is coupled to first and second linkage elements 20, 22 which in turn are coupled to a trigger 18 (FIG. 1B). One end of the trigger 18 can be pivotally mated to the housing 16 to allow the trigger 18 to pivot toward and away from the housing 16 to move between closed and open positions, respectively. The trigger 18 can be biased to an open position, shown in FIG. 1A, due to the wave springs 42, 84 that bias the plates 40, 50, 80, 90 to the open position. In use, as the trigger 18 is compressed toward the housing 16 (e.g., via a user supplied force), the second linkage arms 20, 22 can pull on the first linkage arm 24 in a proximal direction, thereby pulling the wedge 100 in a proximal direction to force the spreader plates 60, 70 apart. When the force is removed from the external lever 18 (e.g., releasing the lever 18), the spreader plates 60, 70 are allowed to return to their original position which thereby returns each pair of opposed plates 40, 50, 80, 90 to their respective biased, open positions. Those skilled in the art will appreciate that various other components and/or linkages are within the spirit and scope of the present invention.

The trigger 18 can also be adapted to provide slack to the tensioning elements 29, 31 when the actuator 25 is in the first position, and to supply a desired tension to (or to remove slack from) the tensioning elements 29, 31 prior to engaging the elements 29, 31 between respective opposed plates 40, 50, 80, 90. For example, when the trigger 18 is in the initial position, the entire actuator 25 is free to slide distally within the housing 16 to provide slack to the tensioning elements 29, 31, and when the trigger 18 is actuated, an initial force can slide the entire actuator 25 in a proximal direction within the housing 16 such that the tensioning elements 29, 31 are tensioned around the respective pair of plates (i.e., the slack is removed), and an additional force can pull only the wedge 100 in the proximal direction so as to lock the tensioning elements 29, 31 between the respective pairs of plates 40, 50, 80, 90. More specifically, looking at FIGS. 1A and 3C, a set of grooves 77B can be incorporated into an inner portion of the housing 16 and they can be configured to receive a corresponding portion 77A of the spreader plates 60, 70 to allow the actuator 25 to slide within the housing 16. The actuator 25 can be biased to a distal portion of the housing 16. This can result from the wave springs 42, 84 biasing the spreader plates 60, 70 toward one another. Since movement of the wedge 100 within the housing 16 is limited by the trigger 18, as the spreader plates 60, 70 are moved together by the wave springs 42, 84, the entire actuator 25 (except the wedge 100) will move within the housing relative to the wedge 100. Thus, as the trigger 18 is actuated, the entire actuator 25 slides proximally within the housing 16 until the tension supplied by the tensioning element(s) reaches an amount which prevents the actuator 25 from sliding any further in the proximal direction. While the actuator 25 is prevented from any further proximal movement, the wedge 100 can continue to move in the proximal direction thereby locking the tensioning element(s) 29, 31 therebetween. Those skilled in the art will appreciate that various other mechanisms and/or configurations can be utilized so as to allow the assembly to uniformly slide within the housing 16. Moreover, while this example allows for a single trigger 18 to both tension the tensioning element(s) and secure the elements between respective pairs of opposed plates, those skilled in the art will appreciate that in other embodiments distinct levers and/or trigger assemblies can be utilized to perform these functions.

Figure 4A:
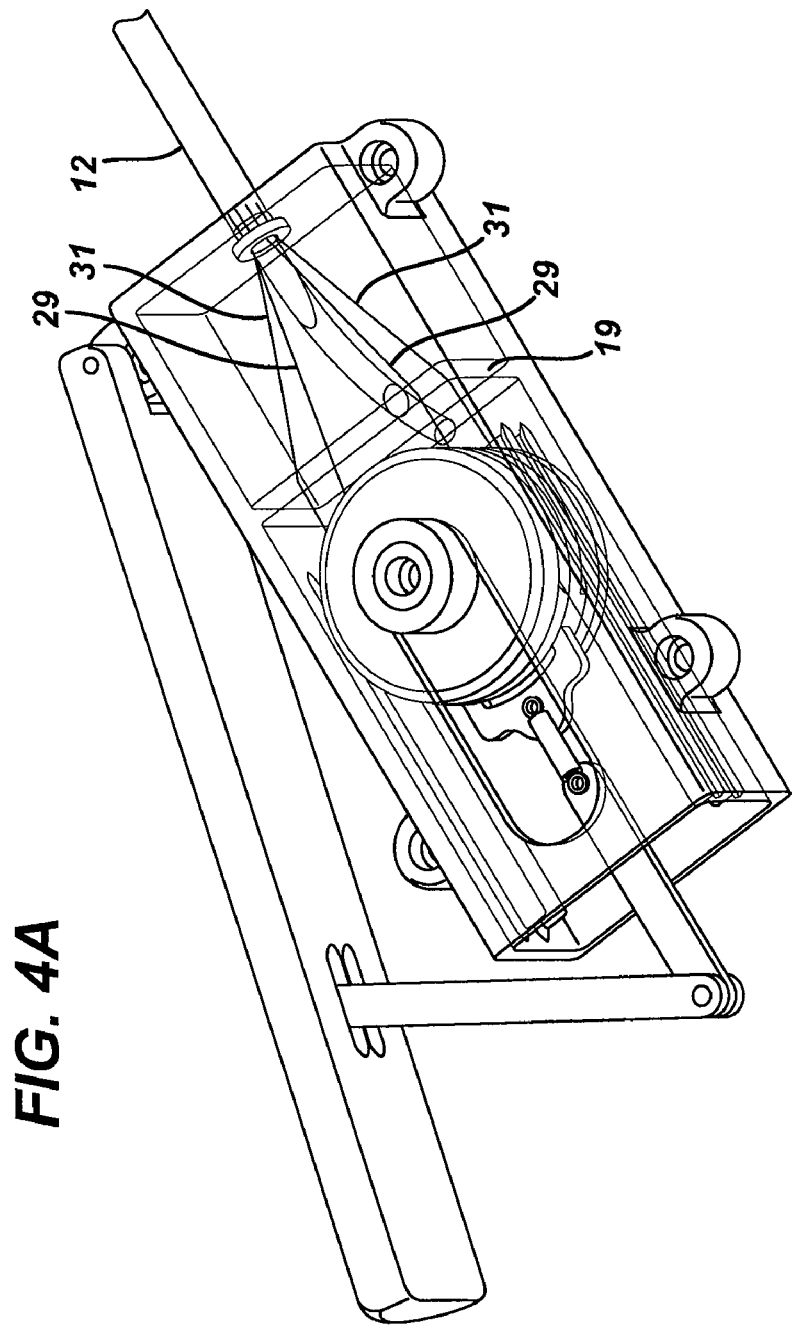
FIG. 4A is a partially transparent isometric view of the handle of FIGS. 1A-1B.
Figure 4B:
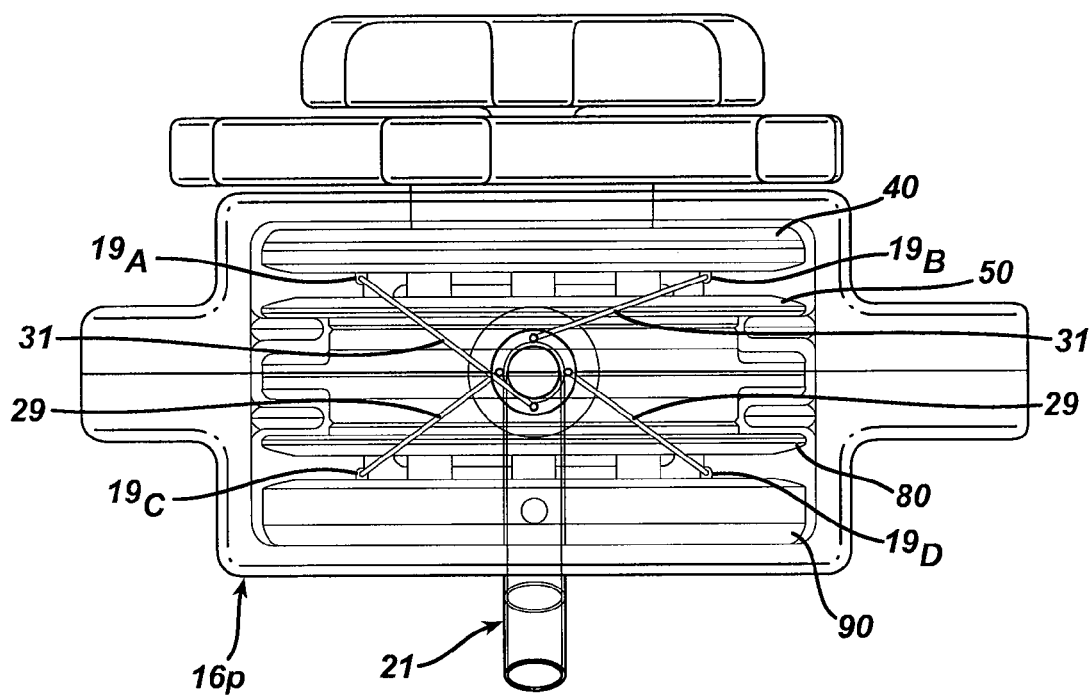
FIG. 4B is a partially transparent rear view of the handle of FIG. 4A.

FIGS. 4A and 4B illustrate the positioning of the tensioning elements 29, 31 relative to the actuator 25. As shown, the first tensioning element 31 can enter the housing 16 and loop around the posts 44 extending between the first pair of opposed plates 40, 50. Likewise, the second tensioning element 29 can also enter the housing 16 and loop around the posts 92 extending between the second pair of opposed plates 80, 90. To provide improved positioning and orientation of the tensioning elements 29, 31, the housing 16 can include an internal guide wall 19 (shown transparently in FIG. 4A) disposed distally of the actuator 25 within the housing 16. The guide wall 19 can include a first pair of openings $19_A$, $19_B$ (FIG. 4B) to allow for passage of first and second portions of the first tensioning element 31, and a second pair of openings $19_C$, $19_D$ to allow for passage of first and second portions of the second tensioning element 29. As such, the guide wall 19 can allow for improved contact and orientation of the tensioning members 29, 31 relative to the actuator 25.

As mentioned above, the device 10 can also include a control mechanism C configured to control axial movement of the tensioning elements 29, 31 to thereby articulate (or otherwise effect an action at) the distal portion 13 of the shaft 12. While various control mechanisms can be used, in one exemplary embodiment, as shown in FIGS. 1A-1C, the top 16' of the housing 16 can include an opening 23 having first and second control members 26, 28 coupled to the actuator 25. In particular, the first and second control members 26, 28 can be coupled to the first and second pair of opposed plates 40, 50, 80, 90, respectively, to allow the control members 26, 28 to apply a rotational force to the plates 40, 50, 80, 90 which in turn will cause axial translations of the tensioning elements 29, 31 engaged therebetween along the length of the shaft 12. Each control member 26, 28 can have a variety of configurations, but in one exemplary embodiment each control member 26, 28 is in the form of a rotational knob. As shown in FIG. 3C, the first control member 26 can have a shaft 26' extending downward and configured to pass through central openings in each of the various components discussed above and illustrated in FIG. 3C. The distal end of the shaft 26' can include a pin-hole 27 that can be aligned with a corresponding pin-hole 93 of the bottom-most plate 90 so as to allow a pin (not shown) to be placed through the corresponding pin-holes 27, 93 to thereby mechanically couple the control member 26 to the second pair of opposed plates 80, 90. The second control member 28 can be rotatably disposed around the shaft 26' of the first control member 26, and it can include a similar pin-hole 35 adapted to be aligned with a pin-hole (not shown) formed in a cylindrical member 41' extending from the top stationary plate 40 and extending into the central opening in the second control member 28. Thus, insertion of a second pin (not shown) through pin-holes will fixedly mate the second control member 28 to the first pair of opposed plates 40, 50. As will be apparent to those skilled in the art, any number of control members can be coupled to any number of corresponding pairs of opposed plates using various mating techniques known in the art.

In use, when the first tensioning element 29 is engaged between the opposed plates 80, 90 (i.e., by moving the trigger 18 to the closed position), rotating the first control knob 26 will cause axial translation of the tensioning element 29 relative to the elongate shaft 12. As a result, one end, e.g., the first end $29_A$, of the first tensioning element 29 will apply a proximally-directed force to the distal portion 13 of the shaft, thereby causing the distal portion 13 to articulate in a first direction (e.g., to the right). Rotation of the control knob 26 in an opposite direction will cause the other end, e.g., the second end $29_B$, of the first tensioning element 29 to apply a proximally-directed force to the distal portion 13 of the shaft, thereby causing the distal portion 13 to articulate in a second, opposite direction (e.g., to the left). The second control knob 28 will similarly cause the second tensioning element 31 to move the distal portion 13 of the shaft 12 in first and second opposite directions. However, since the second tensioning element 31 is positioned radially offset from the first tensioning element 29, the second tensioning element 31 will cause movement of the distal portion 13 of the shaft 12 in a plane that is transverse, or orthogonal in the illustrated embodiment, to the plane within which the distal portion 13 moves in response to movement of the first tensioning element 29. As will be apparent to those skilled in the art, various other embodiments of the device can be utilized for actuating various types of end effectors disposed at the distal end of the device. All such embodiments are within the spirit and scope of the present invention.

Figure 5:
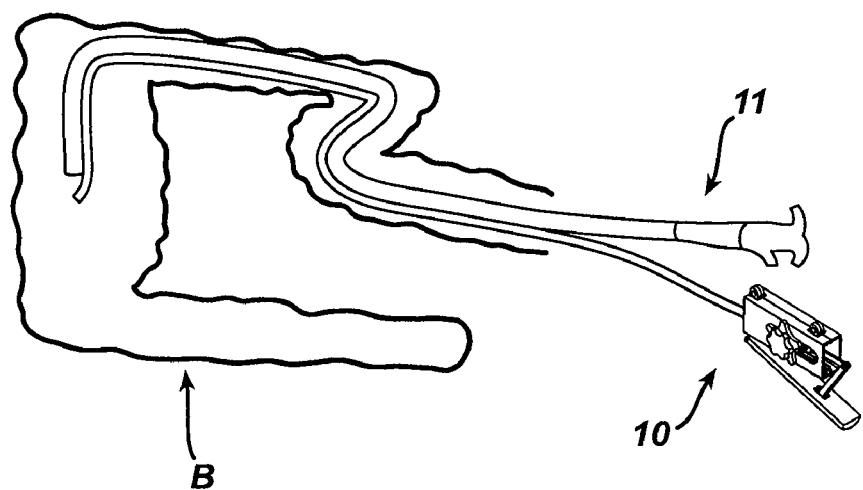
FIG. 5 is an illustration of the device of FIGS. 1A-1B performing an endoscopic procedure.

Methods for controlling tension applied to a tensioning element extending through a flexible endoscopic device are also provided. In one exemplary embodiment, a flexible shaft can be inserted through a tortuous lumen with a tensioning element extending through the shaft being in a slacked position to allow for free flexion of the flexible shaft. Once at a treatment site, the slack can be removed from the tensioning element to allow tension to be applied to the tensioning element to achieve a desired action, such as articulation and/or actuation of a distal portion of the device. The method can be utilized with any type of endoscopic device capable of performing any type of endoscopic procedure. For example, in the exemplary embodiment represented in FIG. 5, the method can include precise articulation of a flexible elongate accessory channel 12 which is coupled to an endoscopic device 11. In such an embodiment, the accessory channel 12 can freely flex as it is inserted through a tortuous body lumen 13 without interference from the tensioning element(s) coupled thereto. Upon arrival at the treatment site, tension can be applied to the tensioning element to supply a desired articulation force to the channel 12 thereby providing precise control of the distal end of the channel 12.

As such, similar to above, a distal portion of the flexible endoscopic device can have a tensioning element coupled thereto for articulating the distal end of the device, and an actuator coupled to the tensioning element. The actuator can be positioned in a first position during insertion such that the tensioning element moves freely relative to the actuator as the flexible elongate shaft is inserted through the tortuous body lumen 13 to allow free movement/flexure of the flexible elongate shaft 12. The actuator can optionally provide slack to the tensioning element in the first position. The method can also include moving the actuator to a second position to cause the actuator to engage the tensioning element, and actuating the actuator to thereby move the tensioning element to cause the tensioning element to actuate the working end of the device so as to controllably articulate at least a portion of the flexible elongate shaft 12 or to actuate an end effector. In one embodiment, moving the actuator to the second position can include pulling a trigger to move a driver disposed adjacent to the actuator. Pulling the trigger can also be effective to slidably move the actuator within a housing to take up any slack in the tensioning element. In another embodiment, actuating the actuator can include rotating a control member coupled to the actuator to rotate the actuator and thereby rotate the tensioning element. In other aspects, the tensioning element can include a first control wire that articulates at least a portion of the flexible elongate shaft in a first plane, and a second control wire that articulates at least a portion of the flexible elongate shaft in a second plate that extends substantially transverse to the first plane.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A control mechanism for an endoscopic device, comprising:
   a tensioning element adapted to extend through a flexible elongate shaft of an endoscopic device;
   a spool having the tensioning element coupled thereto, the spool being movable between a first position in which the spool provides slack to the tensioning element, and a second position in which the spool engages the tensioning element such that movement of the spool is effective to tension the tensioning element; and
   a driver disposed adjacent to the spool and adapted to move the spool between the first and second positions;
   wherein the spool includes opposed plates that are spaced apart from one another in the first position, and that move together to engage the tensioning element in the second position, and wherein the driver comprises a wedge slidably disposed relative to the opposed plates.

2. The control mechanism of claim 1, wherein the wedge is slidably disposed between a pair of spreader plates movably coupled to one another, and wherein sliding movement of the wedge is effective to move the pair of spreader plates toward and away from one another to thereby move the opposed plates between the first and second positions.

3. The control mechanism of claim 1, wherein the wedge is coupled to a trigger disposed on a housing containing the spool and the wedge therein, the trigger being adapted to slidably move the wedge.

4. The control mechanism of claim 1, wherein the spool is slidably disposed within a housing.

5. The control mechanism of claim 1, wherein the spool comprises a pair of plates with a plurality of posts extending therebetween for movably coupling the pair of plates, the tensioning element being at least partially disposed around the plurality of posts.

6. The control mechanism of claim 5, wherein the pair of plates is biased to one of the first and second positions.

7. The control mechanism of claim 1, further comprising a control member coupled to the spool and adapted to rotate the spool to move the tensioning element when the spool is in the second position.

8. The control mechanism of claim 7, wherein the control member comprises a rotatable knob fixedly coupled to the spool.

9. The control mechanism of claim 1, wherein the spool comprises a first spool and the tensioning element comprises a first tensioning element, and wherein the device further includes:
   a second tensioning element adapted to extend through a flexible elongate shaft of an endoscopic device; and
   a second spool having the second tensioning element disposed therebetween, the second spool being movable between a first position in which the second spool provides slack to the second tensioning element, and a second position in which the second spool engages the second tensioning element such that movement of the second spool is effective to tension the second tensioning element.

10. The control mechanism of claim 9, further comprising a driver disposed between the first and second spools and adapted to move the first and second spools between the first and second positions.

11. The control mechanism of claim 10, wherein the driver comprises a wedge slidably disposed between the first and second spools and adapted to move a first plate member on each of the first and second spools toward and away from a second plate member on each of the first and second spools.

12. The control mechanism of claim 1, further comprising a flexible elongate shaft having the tensioning element extending along a length thereof and offset from a central axis of the elongate shaft.

13. A control mechanism for an endoscopic device, comprising:

first and second tensioning elements adapted to extend through a flexible elongate shaft of an endoscopic device;

a first spool having the first tensioning element coupled thereto, the first spool being movable between a first position in which the first spool provides slack to the first tensioning element, and a second position in which the first spool engages the first tensioning element such that movement of the first spool is effective to tension the first tensioning element;

a second spool having the second tensioning element disposed therebetween, the second spool being movable between a first position in which the second spool provides slack to the second tensioning element, and a second position in which the second spool engages the second tensioning element such that movement of the second spool is effective to tension the second tensioning element; and a driver disposed between the first and second spools and adapted to move the first and second spools between the first and second positions;

wherein the driver comprises a wedge slidably disposed between the first and second spools and adapted to move a first plate member on each of the first and second spools toward and away from a second plate member on each of the first and second spools.

* * * * *